United States Patent [19]

Findeisen

[11] 4,430,503

[45] Feb. 7, 1984

[54] PREPARATION OF α-DICYANOTRIMETHYLSILYLOXY COMPOUNDS

[75] Inventor: Kurt Findeisen, Odenthal, Fed. Rep. of Germany

[73] Assignee: Bayer Aktiengesellschaft, Leverkusen, Fed. Rep. of Germany

[21] Appl. No.: 422,514

[22] Filed: Sep. 23, 1982

[30] Foreign Application Priority Data

Oct. 13, 1981 [DE] Fed. Rep. of Germany ....... 3140632

[51] Int. Cl.$^3$ ................................................ C07F 7/10
[52] U.S. Cl. .................................... 556/417; 544/106; 546/14; 548/110; 548/406; 549/505; 549/506
[58] Field of Search ........................ 556/417; 544/106; 546/14; 548/110, 406; 549/505, 506

[56] References Cited

U.S. PATENT DOCUMENTS

| | | | |
|---|---|---|---|
| 3,466,314 | 9/1969 | Moedritzer et al. | 556/417 |
| 3,595,897 | 7/1971 | Brown et al. | 556/417 X |
| 3,658,868 | 4/1972 | Müller et al. | 556/417 X |
| 3,884,954 | 5/1975 | Bakassian | 556/417 X |
| 3,975,422 | 8/1976 | Buck | 556/417 X |

FOREIGN PATENT DOCUMENTS 2067211 12/1980 United Kingdom .

OTHER PUBLICATIONS

W. Lidy et al., Tetrahedron Letters, pp. 1449–1450.

*Primary Examiner*—Paul F. Shaver
*Attorney, Agent, or Firm*—Sprung, Horn, Kramer & Woods

[57] ABSTRACT

A process for preparing partially known α-dicyanotrimethylsilyloxy compounds which are intermediates in the production of insecticidal substituted hydroxymalonic acid diamides and are of the general formula

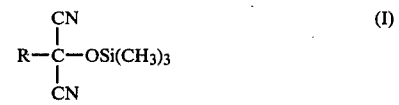

comprises reacting a carboxylic anhydride of the general formula

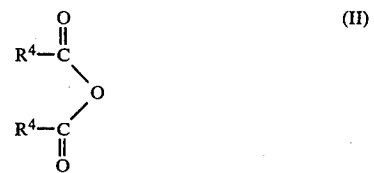

at a temperature between 10° and 250° C. with trimethylsilyl cyanide, if appropriate in the presence of a solvent and/or if appropriate in the presence of a catalyst.

8 Claims, No Drawings

PREPARATION OF α-DICYANOTRIMETHYLSILYLOXY COMPOUNDS

The present invention relates to an unobvious process for preparing certain α-dicyanotrimethylsilyloxy compounds, some of which are known.

It has already become known to synthesize α-dicyanotrimethylsilyloxy compounds by reacting carboxylic acid chlorides with trimethylsilyl cyanide. (Chem. Ber. 106, 587 (1973); Tetrahedron Letters No. 17, pages 1449–1450 (1973)).

The present invention now provides a process for the preparation of an α-dicyanotrimethylsilyloxy compound of the general formula $$R-\underset{CN}{\overset{CN}{C}}-OSi(CH_3)_3 \quad (I)$$

in which

R represents an optionally substituted alkyl group having 1 to 8 carbon atoms, an optionally substituted cycloalkyl group having 3 to 12 carbon atoms, an optionally substituted aryl group or an optionally substituted 5- or 6-membered heterocyclic ring, which can additionally be fused with a benzene ring, or a radical of the general formula

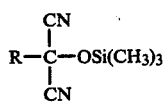

in which

R¹ and R² are identical or different and represent a hydrogen atom, an optionally substituted alkyl group having 1 to 8 carbon atoms or together with the adjacent carbon atoms form a cycloaliphatic ring having 1 to 5 carbon atoms or together with the adjacent carbon atoms represent an aromatic or heteroaromatic ring and R³ represents a hydrogen or halogen atom or a nitro, alkoxy or carbalkoxy group, a cyclic anhydride radical, an optionally substituted alkyl group having 1 to 8 carbon atoms, an optionally substituted cycloalkyl group which is optionally fused with the aromatic ring formed by R¹ and R², optionally substituted aryl radical which is optionally fused with the aromatic ring formed by R¹ and R², or an optionally substituted 5- or 6-membered heterocyclic radical which is optionally fused with the aromatic ring formed by R¹ and R², characterized in that a carboxylic anhydride of the general formula

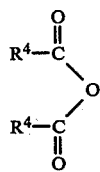

(II)

in which the radicals

R⁴ represent an optionally substituted alkyl radical having 1 to 8 carbon atoms, an optionally substituted cycloalkyl radical having 3 to 12 carbon atoms, an optionally substituted aryl radical or an optionally substituted 5- or 6-membered heterocyclic ring, which can additionally be fused with a benzene ring, or both radicals R⁴ together represent a radical of the general formula

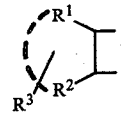

in which

R¹, R² and R³ have the meanings indicated above, is reacted at a temperature between 10° and 250° C. with trimethylsilyl cyanide, if appropriate in the presence of a solvent and/or if appropriate in the presence of a catalyst.

It is surprising that α-dicyanotrimethylsilyloxy compounds of the general formula (I) can be obtained by the process according to the invention in high yield and excellent purity. Thus, for example, the reaction of cyclic aromatic carboxylic anhydrides of the formula (II) with anhydrous hydrocyanic acid is not successful.

The process according to the invention has a number of advantages. For instance, it is not restricted to the synthesis of a few certain compounds but it is widely applicable. Furthermore, the process according to the invention produces α-dicyanotrimethylsilyloxy compounds in high yield and excellent purity.

An additional critical advantage of the process according to the invention is that working up causes no problems. The trimethylsilyl esters resulting in the course of the reaction can readily be separated by distillation from the α-dicyanotrimethylsilyloxy compounds.

If benzoic anhydride and trimethylsilyl cyanide are used as starting materials, the course of the reaction according to the invention is illustrated by the following equation:

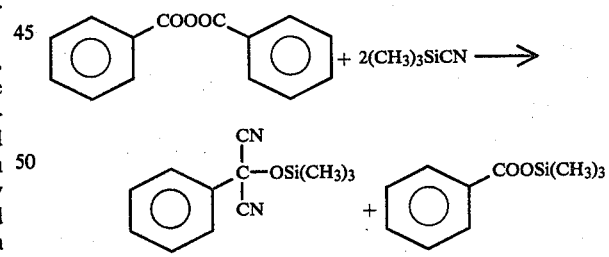

If phthalic anhydride and trimethylsilyl cyanide are used as starting materials, the course of the reaction according to the invention is illustrated by the following equation:

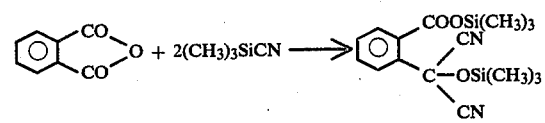

Acid anhyrides of formula (II) used as starting materials are known and can be prepared by known methods.

In formula (II), $R^4$ preferably represents straight-chain or branched alkyl having 1 to 4 carbon atoms, and each of these alkyl radicals can be substituted by alkoxy having 1 to 4 carbon atoms, carbalkoxy having 1 to 4 carbon atoms in the alkoxy group, nitro, nitrile and/or halogen, such as fluorine, chlorine or bromine. $R^4$ also preferably represents cycloalkyl which has 5 or 6 carbon atoms in the ring system and may be substituted by alkyl, alkoxy or carbalkoxy, each of which has up to 4 carbon atoms, nitro, nitrile and/or halogen, such as fluorine, chlorine or bromine. Moreover, $R^4$ preferably represents aryl, in particular phenyl or naphthyl, which may be substituted by alkyl, alkoxy or carbalkoxy, each of which has up to 4 carbon atoms, nitro and/or halogen, for example, fluorine, chlorine or bromine. $R^4$ finally preferably represents 5- or 6-membered heterocyclic radicals which can contain 1 to 3 heteroatoms, such as oxygen, sulphur and/or nitrogen, in the ring and which can additionally be fused with a benzene ring and which can be substituted by alkyl, alkoxy or carbalkoxy, each of which has up to 4 carbon atoms, nitro, nitrile and/or halogen, for example, fluorine, chlorine or bromine.

Examples which may be mentioned of possible heterocyclic radicals are morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

In the case where, in the formula (II), the two radicals $R^4$ represent the radical

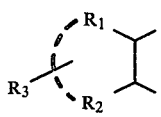

$R^1$ and $R^2$ are preferably identical or different and represent in particular hydrogen, an optionally substituted alkyl radical having 1 to 8 carbon atoms or together represent a cycloaliphatic ring having 1 to 5 carbon atoms or together represent an aromatic or heterocyclic ring. $R^3$ preferably represents hydrogen, halogen, such as fluorine, chlorine or bromine, nitro, alkoxy having 1 to 4 carbon atoms, carbalkoxy having 1 to 6 carbon atoms, cyclic anhydride, straight-chain or branched alkyl having 1 to 8 carbon atoms, cycloalkyl having 5 or 6 carbon atoms in the ring system, which can be fused with the aromatic, 5- or 6-membered heterocyclic radicals which can contain 1 to 3 hetero-atoms, such as oxygen, sulphur and/or nitrogen in the ring and can additionally be fused with a benzene ring and which may be substituted by alkyl, alkoxy or carbalkoxy, each of which has up to 4 carbon atoms, nitro, nitrile and/or halogen, such as fluorine, chlorine or bromine. Examples which may be mentioned of preferred possible aromatic radicals are phenyl and naphthyl, in particular phenyl.

Examples which may be mentioned of preferred possible heterocyclic radicals are morpholinyl, imidazolyl, pyrazolyl, pyrrolyl, isoxazolyl, piperidinyl, oxazolyl, 1,2,4-triazol-1-yl, 1,2,4-triazol-4-yl, 1,2,3-triazolyl, 1,2,4-thiadiazol-2-yl, benzimidazolyl and furanyl.

Preferred examples which may be mentioned in detail of acid anhydrides of the formula (II) are acetic anhydride, propionic anhydride, pivalic anhydride, cyclohexanoic anhydride, benzoic anhydride, m-chlorobenzoic anhydride, p-chlorobenzoic anhydride, 3,5-dichlorobenzoic anhydride, naphthalene-1-carboxylic acid anhydride and 1-phenyl-5-pyrazolone-3-carboxylic acid anhydride. Particularly preferred anhydrides which may be mentioned in particular are benzoic anhydride and pivalic anhydride.

Further preferred examples of cyclic aliphatic, cycloaliphatic, aromatic or, hetero-aromatic carboxylic acid anhydrides of the formula (II) may be mentioned: succinic anhydride, glutaric anhydride, cyclopentanedicarboxylic acid anhydride, hexahydrophthalic anhydride, tetrahydrophthalic anhydride, phthalic anhydride, 4-nitrophthalic anhydride, 4-chlorophthalic anhydride, 3-chlorophthalic anhydride, 4-hydroxyphthalic anhydride, naphthalic anhydride, pyromellitic dianhydride, trimellitic anhydride and pyridinedicarboxylic acid anhydride. The aromatic carboxylic anhydrides of formula (II) are particularly preferred starting materials.

Possible diluents which can be used when carrying out the process according to the invention are any of the inert organic solvents which do not chemically react either with the carboxylic acid anhydrides or with trimethylsilyl cyanide. Examples of such solvents are xylenes, such as o-xylene, chlorobenzene, o-dichlorobenzene, the trichlorobenzenes, nitrobenzene and tetramethylene sulphone. However, in principle it is also possible to carry out the reaction according to the invention without a diluent.

The reaction temperature can be varied within the mentioned relatively wide range, i.e. the reaction is carried out at a temperature between 10° and 250° C., preferably between 80° and 190° C.

The reaction is generally carried out under atmospheric pressure. However, when low-boiling, aliphatic carboxylic acid anhydrides are used a slight overpressure is advantageous, and it then is 1 to 10, preferably 1 to 5, atmospheres.

The reaction rate can be accelerated by the addition of catalytic amounts of Lewis acids. Examples which may be mentioned of suitable Lewis acids are zinc chloride, zinc cyanide, copper(I) cyanide, zinc iodide, aluminum chloride and boron trifluoride.

When carrying out the process according to the invention, one mol of acid anhydride is generally reacted with two mols of trimethylsilyl cyanide.

After the reaction is complete, the reaction product is customarily worked up by distillation and, if necessary, recrystallization.

The mixture of acid anhydride and trimethylsilyl cyanide can, according to the invention, also be reacted in the gas phase without special application of catalysts.

It is also possible to design the process according to the invention to be continuous.

The α-dicyanotrimethylsilyloxy compounds which are readily producible by the process according to the invention can be used, for example, in the synthesis of insecticides. Thus, for example, substituted hydroxymalonic acid diamides, highly potent insecticidal compounds, can be prepared from the compounds according to the invention, by hydrolysis for example in accordance with the following equation:

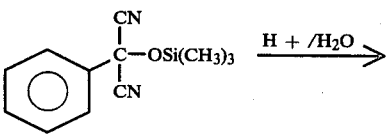

-continued

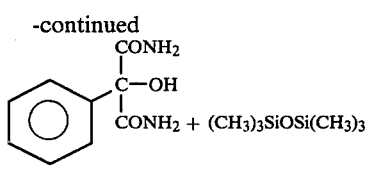

The substituted hydroxymalonic acid diamides and their use as insecticides does not yet belong to the state of the art but forms the subject of copending Application Ser. No. 419,100, filed Sept. 16, 1982, now pending (corresponding to German application P No. 31 40 275.5, filed Oct. 10, 1981, Le A 21 341).

PREPARATIVE EXAMPLES

EXAMPLE 1

In a 500 ml four-necked flask equipped with a stirrer, thermometer, reflux condenser and dropping funnel, 226 g of benzoic anhydride (1 mol) were heated at 170° C., and 200 g of trimethylsilyl cyanide (2 mols) were added dropwise in the course of three hours. The mixture was then stirred for thirty minutes at this temperature and, after cooling down, fractionally distilled.

Yield: 222 g of dicycano-(phenyl)-trimethylsiloxy)-methane (=97% of theory).

Boiling point: 128°-129° C./14 mbar.

EXAMPLE 2

In a 500 ml three necked flask, 186 g of pivalic anhydride (1 mol), 198 g of trimethylsilyl cyanide (2 mols) and 1 g of zinc chloride were heated from initially 140° C. in the course of three hours to 170° C. The anhydride bands had disappeared in the IR spectrum. After cooling down, the mixture was fractionally distilled. Yield: 193 g of dicyano-(tert.-butyl)-(trimethylsiloxy)-methane (=92% of theory).

Boiling point: 70°-72° C./16 mbar.

The following α-dicyanotrimethylsilyloxy compounds were synthesized according to Examples 1 and 2:

TABLE 1

| No. | Starting product | Final product | Yield (%) | Boiling point (°C.) (mbar) |
|---|---|---|---|---|
| 3 | (3,6-dichlorobenzoic anhydride)₂ | 3,6-Cl₂-C₆H₃-C(CN)₂-OSi(CH₃)₃ | 87 | 113-116/0.2 Melting point 62-64 |
| 4 | (CH₃CO)₂O | CH₃-C(CN)₂-OSi(CH₃)₃ | 84 | 62-64/18 |
| 5 | (CH₃CH₂-CO)₂O | CH₃-CH₂-C(CN)₂-OSi(CH₃)₃ | 89 | 63-65/18 |
| 6 | (4-CH₃-C₆H₄-CO)₂O | 4-CH₃-C₆H₄-C(CN)₂-OSi(CH₃)₃ | 94 | 140-143/18 |
| 7 | (4-Cl-C₆H₄-CO)₂O | 4-Cl-C₆H₄-C(CN)₂-OSi(CH₃)₃ | 93 | 147-149/16 |
| 8 | (3,5-Cl₂-C₆H₃-CO)₂O | 3,5-Cl₂-C₆H₃-C(CN)₂-OSi(CH₃)₃ | 91 | 119-121/0.2 |
| 9 | (3-Cl-C₆H₄-CO)₂O | 3-Cl-C₆H₄-C(CN)₂-OSi(CH₃)₃ | 97 | 143-146/16 |

TABLE 1-continued

| No. | Starting product | Final product | Yield (%) | Boiling point (°C.) (mbar) |
|---|---|---|---|---|
| 10 | (3,4-dichlorobenzoyl)₂O | 3,4-dichlorophenyl-C(CN)₂-OSi(CH₃)₃ | 93 | 113–116/0.1 |
| 11 | (2-chlorobenzoyl)₂O | 2-chlorophenyl-C(CN)₂-OSi(CH₃)₃ | 91 | 107–110/0.2 |
| 12 | (2,4-dichlorobenzoyl)₂O | 2,4-dichlorophenyl-C(CN)₂-OSi(CH₃)₃ | 88 | 126–130/0.2 |
| 13 | (4-nitrobenzoyl)₂O | 4-nitrophenyl-C(CN)₂-OSi(CH₃)₃ | 86 | 153–156/0.5 |
| 14 | (4-methoxybenzoyl)₂O | 4-methoxyphenyl-C(CN)₂-OSi(CH₃)₃ | 98 | 140–142/0.5 |
| 15 | (3-trifluoromethylbenzoyl)₂O | 3-trifluoromethylphenyl-C(CN)₂-OSi(CH₃)₃ | 91 | 117–119/16 |
| 16 | (1-naphthoyl)₂O | 1-naphthyl-C(CN)₂-OSi(CH₃)₃ | 87 | 157–160/0.5 |
| 17 | (4-biphenylcarbonyl)₂O | 4-biphenyl-C(CN)₂-OSi(CH₃)₃ | 91 | 165–170/0.3 |
| 18 | (5-methylisoxazol-3-carbonyl)₂O | 5-methylisoxazol-3-yl-C(CN)₂-OSi(CH₃)₃ | 93 | 136–138/16 |

TABLE 1-continued

| No. | Starting product | Final product | Yield (%) | Boiling point (°C.) (mbar) |
|---|---|---|---|---|
| 19 | (cyclohexyl-H-CO)₂O | cyclohexyl-H-C(CN)(CN)-OSi(CH₃)₃ | 98 | 123-125/16 |
| 20 | (CH₃-C(CH₂F)(CH₂F)-CO)₂O | CH₃-C(CH₂F)(CH₂F)-C(CN)(CN)-OSi(CH₃)₃ | 91 | 97-100/16 |
| 21 | (CH₃OCH₂—CO)₂O | CH₃OCH₂-C(CN)(CN)-OSi(CH₃)₃ | 88 | 98-100/18 |
| 22 | (CCl₃—CO)₂O | CCl₃-C(CN)(CN)-OSi(CH₃)₃ | 90 | 90-92/14 |
| 23 | (ClCH₂-C(CH₃)(CH₃)-CO)₂O | ClCH₂-C(CH₃)(CH₃)-C(CN)(CN)-OSi(CH₃)₃ | 91 | 104-106/16 |
| 24 | (F₃CO-C₆H₄-CO)₂O | F₃CO-C₆H₄-C(CN)(CN)-OSi(CH₃)₃ | 87 | 129-132/18 |

EXAMPLE 25

In a 500 ml four-necked flask equipped with a stirrer, thermometer, reflux condenser and dropping funnel, 148 g of phthalic anhydride (1 mol) were heated to 180° C., one gram of aluminum chloride was added, and 200 g of trimethylsilyl cyanide (2.02 mols) were added (at this temperature) dropwise in the course of two hours. The mixture was then stirred for one hour. The reaction product was fractionally distilled.

Yield: 318 g of {dicyano-[(2-trimethylsiloxycarbonyl)-phenyl]-methoxy}-trimethylsilane (=92% of theory).

Boiling point: 145°-147° C./0.3 mbar.

The first runnings contained unreacted phthalic anhydride.

EXAMPLE 26

In a 500 ml three-necked flask equipped with a stirrer, thermometer and reflux condenser, 154 g of hexahydrophthalic anhydride (1 mol) were mixed with 198 g of trimethylsilyl cyanide (2 mols) at room temperature, and the internal temperature was raised in the course of one hour to 110° C. Stirring was then continued at this temperature for three hours. The reaction product could be used without further purification.

Yield: 348 g of }dicyano-[(2-trimethylsiloxycarbonyl)-cyclohexyl)]-methoxy}-trimethylsilane (=99% of theory)

Boiling point: 134°-136° C./0.45 mbar.

EXAMPLE 27

In a 500 ml three-necked flask equipped with a stirrer, thermometer and reflux condenser, 114 g of glutaric anhydride (1 mol) and 198 g trimethylsilyl cyanide (2 mols) were mixed. This resulted in a slightly exothermic reaction up to 40° C. After 2 hours, the internal temperature was raised to 70° C., and the mixture was left for three hours at this temperature. The reaction product was fractionally distilled.

Yield: 294 g of {dicyano-[(2-trimethylsiloxycarbonyl)propyl]-methoxy}-trimethylsilane (=94% of theory).

Boiling point: 103°-105° C./0.2 mbar.

EXAMPLE 28

In a 750 ml four-necked flask equipped with a stirrer, thermometer, reflux condenser and dropping funnel, 218 g of pyromellitic dianhydride (1 mol) and 198 g of trimethylsilyl cyanide (2 mols) were heated at 120° C. After about one hour, the internal temperature had increased to 160° C., and 198 g of trimethylsilyl cyanide (2 L mols) were added dropwise at this temperature in the course of a further two hours. The reaction was monitored by IR spectroscopy. After the anhydride had almost completely reacted, the reaction was terminated. The reaction product was recrystallized from a small amount of cyclohexane.

Yield: 527 g

Melting point: 211°-212° C.

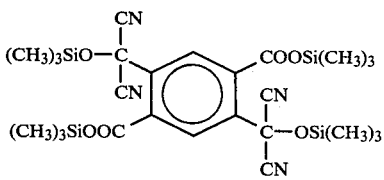

EXAMPLE 29

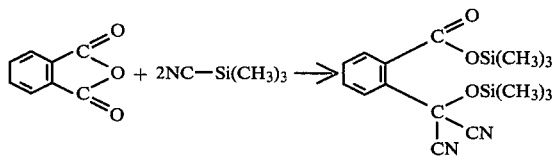

148 g (1 mol) of phthalic acid anhydride are initially introduced into a reaction vessel with 2 g of sodium cyanide and 198 g (2 mols) of trimethylsilyl cyanide are added slowly. The exothermic reaction is kept at 60° C. by cooling with ice. After stirring for 15 minutes the reaction mixture becomes a clear slightly yellow solution. The spectroscopic examination by means of IR and KR showed a pure reaction product. b.p. 0.2 mbar: 145°–147° C., quantity: 335.6 g Yield: 97% of theory

EXAMPLE 30

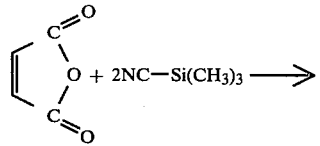

198 g (2 mols) of trimethylsilyl cyanide and 1 g of triethylenediamine are initially introduced into a reaction vessel. 98 g (1 mol) of maleic acid anhydride are then introduced at a temperature kept at 40°–50° C. by cooling with ice. The reaction mixture is stirred for a further 30 minutes and distilled. b.p.$_{0.6\ mbar}$: 125°–126° C., quantity: 269.4 g Yield: 91% of theory

EXAMPLE 31

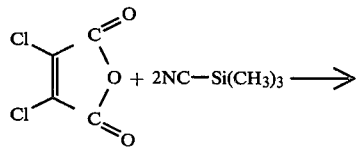

198 g (2 mols) of trimethylsilyl cyanide and 2 ml of N,N-dimethylbenzylamine are initially introduced into the reaction vessel and 167 g (1 mol) of dichloromaleic acid anhydride are added while stirring. The exothermic reaction is kept at 40°–50° C. by cooling with ice. The mixture is purified by distillation.

I b.p.$_{20\ mbar}$: 95°–120° C., quantity: 82 g
  GC: 95% of dichloromaleic acid anhydride 4.5% of reaction product
II b.p.$_{20\ mbar}$: 148°–152° C., quantity 191.4 g
  GC: 98.5% of reaction product
  Yield according to GC: 53.4% of theory

EXAMPLE 32

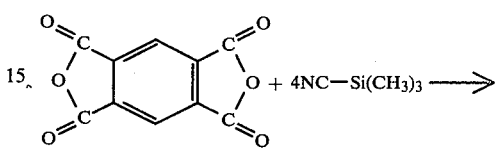

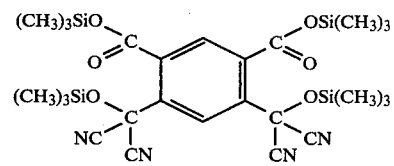

109 g (0.5 mol) of benzene-1,2,4,5-tetracarboxylic acid dianhydrde are mixed with 198 g (2 mols) of trimethylsilyl cyanide and 2 ml of triethylamine. The exothermic reaction is kept at 40°–50° C. by cooling with ice. The reaction mixture becomes solid.

The product is purified by recrystallization from cleaning benzine.

Quantity: 239.5 g, m.p. 203°–205° C.
Yield: 78% of theory

EXAMPLE 33

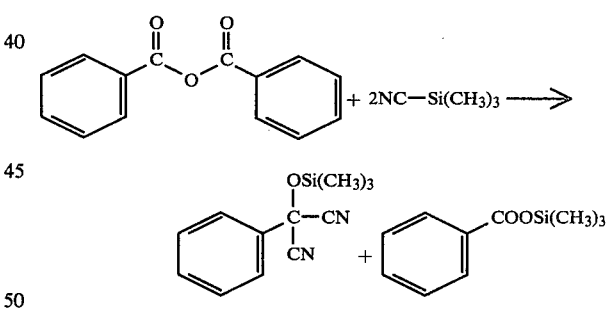

113 g (0.5 mol) of benzoic acid anhydride, 1 g of triethylene diamine and 99 g (1 mol) of trimethylsilyl cyanide are mixed while stirring. The exothermic reaction exhibits a rise in temperature to 48° C. Stirring is continued for 30 minutes at 40°–50° C. and the reaction mixture is distilled.

I b.p.$_{14\ mbar}$: 96°–98° C., quantity 95 g
II b.p.$_{14\ mbar}$: 128°–130° C., quantity: 112.7 g
Yield:
  98% of theory of dicyano-(phenyl)-(trimethylsiloxy)-methane
  97.8% of theory of benzoic acid trimethylsilyl ester The following examples illustrate the further reaction of the compounds which can be prepared according to the invention to give the insecticidal substituted hydroxymalonic acid diamides.

EXAMPLE 34

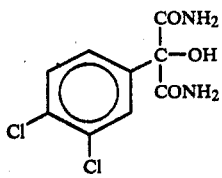

600 g of sulphuric acid (96% strength) were initially introduced into a 1 liter four-necked flask equipped with a reflux condenser, stirrer, thermometer and dropping funnel and externally cooled. 299 g of 3,4-dichlorophenyltrimethylsilyloxymalonic acid dinitrile (1 mol) were then added dropwise in the course of 30 minutes, during which the internal temperature was not allowed to exceed 50° C., into the sulphuric acid. After the exothermic reaction was complete, stirring was continued for 15 minutes. The reaction mixture was poured into ice-water, and the reaction product precipitated, was filtered off with suction, washed until neutral and dried, and the residue was recrystallized from ethanol.

Yield: 242 g of 3,4-dichlorophenylhydroxymalonic acid diamide (=92% of theory).
Melting point: 175°–177° C.

EXAMPLE 35

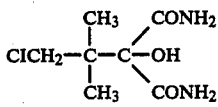

As described in Example 34, 200 g of sulphuric acid (96% strength) were initially introduced, and a mixture of 244 g of chloro-tert.-butyltrimethylsilyloxymalonic acid dinitrile (1 mol), dissolved in 150 ml of methylene chloride at 0° to 5° C., was added dropwise. Cooling was then removed, and the internal temperature rose to 30° C. After 30 minutes, the mixture was briefly heated at the reflux temperature of the methylene chloride. The methylene chloride was removed by distillation, and the residue was stirred into 2 liters of ice-water. The precipitated product was filtered off with suction, washed with water until neutral, dried and recrystallized from ethanol.

Yield: 181 g of chloro-tert.-butylhydroxylmalonic acid diamide (=87% of theory)
Melting point: 183°–185° C.

EXAMPLE 36

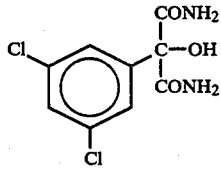

As described in Example 1, 200 g of sulphuric acid (96% strength) were initially introduced, and 98 g of 3,5-dichlorophenyltrimethylsilyloxymalonic acid dinitrile (0.33 mol) were added dropwise with cooling at 40° to 50° C. Stirring was then continued for one hour at 60° C. The reaction mixture was added to warm water at 50° to 60° C., and the precipitate was filtered off with suction, washed until neutral and recrystallized from acetonitrile.

Yield: 75 g of 3,5-dichlorophenylhydroxymalonic acid diamide (=87% of theory).
Melting point: 181°–183° C.

The insecticidal activity of the substituted hydroxymalonic acid diamides which can be prepared from the intermediates of formula (I) obtained by the process of the present invention is illustrated by the following biotest example:

EXAMPLE 37

Phaedon larvae test
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Cabbage leaves (Brassica oleracea) were treated by being dipped into the preparation of the active compound of the desired concentration and were infested with mustard beetle larvae (Phaedon cochleariae), as long as the leaves were still wet.

After the specified periods of time, the destruction in % was determined. 100% meant that all the beetle larvae had been killed; 0% meant that none of the beetle larvae had been killed.

In this test, the substituted hydroxymalonic acid diamides show high activity.

It will be understood that the specification and examples are illustrative but not limitative of the present invention and that other embodiments within the spirit and scope of the invention will suggest themselves to those skilled in the art.

I claim:

1. A process for the preparation of an α-dicyanotrimethylsilyloxy compound of the formula

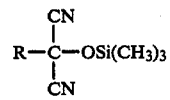

in which
R represents an optionally substituted alkyl group having 1 to 8 carbon atoms, an optionally substituted cycloalkyl group having 3 to 12 carbon atoms, an optionally substituted aryl group or an optionally substituted 5- or 6-membered heterocyclic ring, which can additionally be fused with a benzene ring, or a radical of the formula

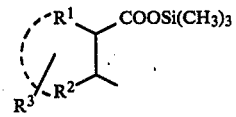

in which
$R^1$ and $R^2$ are identical or different and represent a hydrogen atom, an optionally substituted alkyl group having 1 to 8 carbon atoms or together with the adjacent carbon atoms form a cycloaliphatic ring having 1 to 5 carbon atoms or together with the adjacent carbon atoms represent an aromatic or heteroaromatic ring and R³ represents a hydrogen or halogen atom or a nitro, alkoxy or carbalkoxy group, a cyclic anhydride radical, an optionally substituted alkyl group having 1 to 8 carbon atoms, an optionally substituted cycloalkyl group which is optionally fused with the aromatic ring formed by R¹ and R², an optionally substituted aryl radical which is optionally fused with the aromatic ring formed by R¹ and R², or an optionally substituted 5- or 6-membered heterocyclic radical, which is optionally fused with the aromatic ring formed by R¹ and R², comprising reacting a carboxylic acid anhydride of the formula

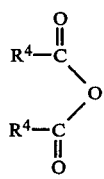

in which the radicals

R⁴ represents an optionally substituted alkyl radical having 1 to 8 carbon atoms, an optionally substituted cycloalkyl radical having 3 to 12 carbon atoms, an optionally substituted aryl radical or an optionally substituted 5- or 6-membered heterocyclic ring, which can additionally be fused with a benzene ring, or both radicals R⁴ together represent a radical of the formula

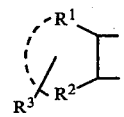

with trimethylsilyl cyanide at a temperature between about 10° and 250° C.

2. A process according to claim 1, wherein the reaction is carried out in the presence of a solvent.

3. A process according to claim 2, wherein the solvent is an inert organic solvent which does not react chemically either with the carboxylic acid anhydride or with trimethylsilyl cyanide.

4. A process according to claim 1, wherein the reaction is carried out in the presence of a catalyst.

5. A process according to claim 4, wherein the catalyst is a Lewis acid.

6. A process according to claim 1, wherein the reaction is carried out at a temperature between about 80° and 190° C.

7. A process according to claim 1, wherein the carboxylic acid anhydride is an aromatic carboxylic acid anhydride.

8. A process according to claim 3, wherein the carboxylic acid anhydride is an aromatic carboxylic acid anhydride and the reaction is carried out at a temperature between about 80° and 190° C. in the presence of a Lewis acid as catalyst.

* * * * *